United States Patent [19]

Portner et al.

[11] 4,083,367
[45] Apr. 11, 1978

[54] METHOD AND APPARATUS FOR PULMONARY FUNCTION ANALYSIS

[75] Inventors: Peer M. Portner, Berkeley; David H. LaForge, Kensington, both of Calif.

[73] Assignee: Andros Incorporated, Berkeley, Calif.

[21] Appl. No.: 709,428

[22] Filed: Jul. 28, 1976

[51] Int. Cl.² .............................................. A61B 5/08
[52] U.S. Cl. .................................. 128/2.07; 128/2.08; 250/343; 356/51; 356/188
[58] Field of Search .................... 128/2.07, 2.08, 2 C, 128/2 L; 356/51, 188; 250/343, 344, 345

[56] References Cited

U.S. PATENT DOCUMENTS

| 2,668,471 | 2/1954 | Benzinger et al. | 128/2.08 X |
| 2,765,409 | 10/1956 | Hutchins et al. | 250/343 |
| 3,171,027 | 2/1965 | Wallack | 250/343 |
| 3,678,262 | 7/1972 | Herrmann | 250/343 X |
| 3,718,135 | 2/1973 | Diamond et al. | 128/2.08 |
| 3,759,249 | 9/1973 | Fletcher | 128/2.08 |
| 3,790,797 | 2/1974 | Sternberg et al. | 250/345 |
| 3,792,272 | 2/1974 | Harte et al. | 250/343 |
| 3,832,548 | 8/1974 | Wallack | 250/343 |
| 3,896,792 | 7/1975 | Vail et al. | 128/2.07 |
| 3,911,276 | 10/1975 | Bell | 250/343 |
| 3,916,195 | 10/1975 | Burch et al. | 250/345 |

OTHER PUBLICATIONS

"The Beckman Bulletin", vol. II, No. 2, 1967, pp. 1 & 7.

*Primary Examiner*—Robert W. Michell
*Assistant Examiner*—Lee S. Cohen
*Attorney, Agent, or Firm*—Fitch, Even, Tabin & Luedeka

[57] ABSTRACT

A method and apparatus for analyzing pulmonary function including diffusing capacity and cardiac output or local pulmonary blood flow while necessarily determining alveolar volume in order to complete the abovenoted analysis. In order to provide a rapid response in each of the abovenoted analyses or determinations, appropriate gases are caused to be inhaled and exhaled through a sample cell wherein a percentage of each gas may be constantly monitored during inhalation and exhalation by means of non-dispersive infrared absorption techniques, the sample cell and associated components of the pulmonary function analyzing device including additional features to facilitate the abovenoted analyses and determinations, the combination of gases employed for monitoring the pulmonary functions being selected to permit accurate detection by infrared absorption techniques.

20 Claims, 6 Drawing Figures

| FILTER | | WAVELENGTH |
|---|---|---|
| A | ZERO REF. | BLANK |
| B | $CH_4$ SIGNAL | 3.2 μm |
| C | $C_2H_2$ SIGNAL | 3.05 μm |
| D | SPAN REF. | 3.95 μm |
| E | $H_2O$ SIGNAL | 2.6 μm |
| F | CO SIGNAL | 4.65 μm |

METHOD AND APPARATUS FOR PULMONARY FUNCTION ANALYSIS

BACKGROUND OF THE INVENTION

The present invention relates to a method and apparatus for analyzing pulmonary functions and more particularly to such a method and apparatus wherein the functions are analyzed through simultaneous infrared radiation monitoring of a plurality of gases, each selected in accordance with its ability to indicate a separate one of the pulmonary functions.

The analysis of gases being inhaled or exhaled from the lungs has long been employed in the assessment of various pulmonary functions. Possibly the most important or basic of these functions includes the determination of alveolar volume or capacity. This function in itself provides an indication as to the condition of the lungs and in addition is essential for the proper measurement or analysis of additional functions such as pulmonary diffusing capacity and cardiac output as manifested in pulmonary blood flow. However, the techniques employed for monitoring these functions have been time consuming while requiring substantial and generally immobile equipment tending to prevent or impair the ability to fully assess various pulmonary functions. In order to provide a more accurate background for the present invention, the general techniques for assessing each of these functions are described briefly below followed by a discussion of problems presently existing in the prior art which prevent the maximum utilization of pulmonary function analysis.

As indicated above, the measurement of alveolar volume may be employed to assess pulmonary function and in itself provides an index of the severity, or at least changes in severity, of certain patterns of pulmonary function. In addition, an accurate determination of lung volume is essential for the proper understanding of newly recognized patterns of dysfunction which in turn are becoming essential for a number of dynamic (and more substantive) studies of pulmonary function in establishing conditions of health and disease. For example, the measurement of pulmonary diffusing capacity by the single breath method can be no more reliable than the underlying measurement of lung volume. Similarly, the single breath method of assessing pulmonary blood flow is dependent upon the underlying measurement of lung volume.

A simple and commonly known method for measuring alveolar volume consists in causing a patient to inhale a known concentration of an inert and insoluble gas such as helium or neon. After a short selected period of breath-holding to allow uniform distribution of the inhaled gas throughout the lungs, the breath is exhaled and a sample of the exhaled gas is collected and analyzed to determine the concentration of the inert gas, for example by means of a gas chromatograph or mass spectrometer. The resultant determination of the gas dilution ratio between the inhaled and exhaled gases may be employed along with volume determinations of the inhaled and exhaled gases in order to assess the alveolar volume. However, these techniques for measuring alveolar volume have serious disadvantages.

Initially, gas chromatography techniques may take as much as ten minutes to perform under usual pulmonary function laboratory conditions with the analysis being limited to a selected point in time during exhalation. In addition, the need for a gas collection system and chromatograph tends to preclude mobile mass screening programs.

A mass spectrometer provides an effective and portable system. However, as is discussed in greater detail below, the mass spectrometer is itself expensive and commonly requires the use of expensive, rare isotope gases.

The measurement of the diffusing capacity of the lungs has similarly become a useful technique in the diagnosis of pulmonary vascular obstruction, pulmonary fibrosis and subclinical emphysema and accordingly may be used as a screening test for determining general pulmonary condition. In a single breath method for determining diffusing capacity, the subject or patient inhales to vital capacity a low, non-toxic concentration in air of a suitable gas such as low concentration carbon monoxide along with an insoluble and inert tracer gas as described above in connection with the measurement of lung volume.

After the breath is held for a short selected period of for example ten seconds, the subject exhales into a collection means such as a spirometer. The exhaled gas is sampled after a prescribed volume of exhalation with the concentrations of the two test gases in the expirate being determined, for example, by means of gas chromatography.

In this manner, it is possible to calculate alveolar volume as described above by means of the dilution ratio for the inert gas. At the same time, pulmonary diffusing capacity may be determined from the initial concentration of carbon monoxide inhaled into the lungs and the calculated diffusion of carbon monoxide from the lungs between inhalation and exhalation.

In the abovenoted tests for diffusing capacity, helium and neon have been most frequently employed as the insoluble inert tracer gas. Carbon monoxide is particularly effective in determining the diffusing capacity of the lungs because of its ability to combine with hemoglobin much more effectively than oxygen; hence, the rate of diffusion of carbon monoxide from the lungs is limited only by its ability to pass through the alveolar capillary walls. Because of its high affinity for hemoglobin, carbon monoxide is a particularly suitable gas for investigating pulmonary diffusing capacity and diffusion abnormalities. Other gases may possibly be employed in place of carbon monoxide for this function. For example, cyanide compounds tend to exhibit the same tendencies of absorption in hemoglobin while being limited in their ability to pass through the alveolar capillary walls. However, such cyanide compounds tend to be unstable as to instant form. In particular such cyanide compounds tend to be present with equilibrium amounts of the monomer (CN) and the dimer ($C_2N_2$) as well as its acid form (HCN). Accordingly, such cyanide compounds are difficult to employ within the abovenoted technique which is normally carried out using carbon monoxide.

In connection with the measurement of diffusing capacity, it is noted that the test is relatively simple, noninvasive and painless but does require a skilled operator and expensive equipment to provide reliable data. Since the method also requires collection of an expired alveolar gas sample for subsequent analysis, the diffusing capacity may be determined only for a single point in the expiration profile. Multiple points during a single breath may be analyzed for example with increased complexity by taking multiple samples. However, reproducibility with such a technique is relatively poor.

Accordingly, the sampling requirement within this technique as well as the slow response time of the standard instruments used in the measurements of expired gas concentrations tend to detract from its value as a diagnostic tool in mass screening.

A different but related method for measuring pulmonary diffusing capacity employs a respiratory mass spectrometer with the carbon monoxide being selected as the isotopic form ($^{13}C^{16}O$ or $^{12}C^{18}O$) having the mass numbers of 29 or 30 respectively, to enable ts separation from molecular nitrogen with a mass number of 28, which is identical to that of the common isotope ($^{12}C^{16}O$). This method, which permits continuous measurement of the expired gases, enables a determination of the distribution of the diffusing capacity during a single breath and may thus be employed for obtaining more complex diagnostic information. However, it does require expensive equipment and the use of a rare isotopic form gas of limited availability. These factors tend to make the technique prohibitively expensive for routine clinical use.

The abovenoted methods of assessing diffusing capacity also fail to provide a rapid response for the assessment of the amount of carbon monoxide in the exhaled gas at any instant. Accordingly, these methods of measuring diffusing capacity are inadequate for certain diagnostic purposes, in particular, the determination of diffusing capacity during exercise where the rate of diffusion must be instantly monitored across a substantial profile portion of exhalation.

It has also been known that the analysis of respired gases may be employed to measure cardiac output or local pulmonary blood flow. In particular, it has been known for some time that gaseous acetylene in small concentrations may be measured during inhalation and exhalation, also in a single breath method, to determine the rate of blood flow in the capillary walls of the lungs. This test depends upon the ability of the acetylene gas to readily pass through the alveolar capillary walls while having only limited solubility in blood. Accordingly, the rate at which acetylene is internally absorbed by the body from the lungs depends upon the rate at which blood is made available for its absorption. Here again, acetylene is used in combination with an inert gas of the type discussed above to permit a simultaneous assessment of alveolar volume in order to calculate the actual rate of loss of acetylene from the lungs as determined by pulmonary blood flow.

The abovenoted technique of pulmonary analysis for assessing blood flow has been used only to a limited extent because of the more developed and thus more commonly employed technique, at least to date, of cardiac catheterization based upon oxygen absorption. However, pulmonary testing with acetylene is of particular advantage in that it is noninvasive and may be adapted to provide an instantaneous measurement of blood flow through the gas exchanging surfaces of walls in the lungs.

It may be seen that various techniques are presently known for accomplishing the determination of alveolar volume as well as the determination of pulmonary diffusing capacity and pulmonary blood flow, for example. However, it has not heretofore been possible to rapidly accomplish various combinations of these determinations with simple portable equipment having a rapid response for assessing the particular pulmonary functions across the entire expiration profile.

There has thus been found to remain a need for a method and apparatus for more rapidly and conveniently assessing pulmonary functions such as those noted above in order to permit the use of such tests in routine clinical use for example as a screening tool.

SUMMARY OF THE INVENTION

Accordingly, it is an object of the invention to provide a method and apparatus for accomplishing pulmonary function analysis in a noninvasive manner and with rapid response to facilitate use of the method and apparatus for assessing instantaneous pulmonary functions.

It is a more particular object of the invention to provide such a method and apparatus wherein analysis of the pulmonary functions is accomplished through the monitoring of selected gases during inhalation and exhalation by means of non-dispersive infrared absorption techniques.

It is a more specific object of the invention to provide such a method and apparatus for simultaneously monitoring alveolar volume and pulmonary diffusing capacity, for simultaneously monitoring alveolar volume and pulmonary blood flow, or for simultaneously monitoring the three functions of alveolar volume, plumonary diffusing capacity and pulmonary blood flow.

It is an even more specific object of the invention to provide such a method and apparatus of pulmonary function analysis wherein two or more selected gas components may be monitored by inhalation and exhalation through an infrared analyzer sample cell including means for simultaneously and continuously monitoring the percentages of the selected gases during inhalation and exhalation.

It is a further related object of the invention to provide such a method and apparatus wherein the above-noted sample cell includes means for assessing volume flow during inhalation and exhalation as well as means for assisting in the determination of alveolar volume.

Yet another further related object of the invention is to provide such a method and apparatus wherein the two or more selected gases for monitoring the various pulmonary functions are selected with closely related but distinct bands of infrared absorption to permit their simultaneous monitoring within the sample cell.

Still another object of the invention is to provide such a method and apparatus wherein the sample cell also includes means to adjust for the effective temperature upon the determination of the gas concentrations.

Still another object of the invention is to provide such a method and apparatus including additional means for monitoring the concentration of interferent gases such as water vapor during inhalation and exhalation in order to properly adjust the determinations for the above-noted pulmonary functions.

In summary, the present invention involves the monitoring through infrared radiation techniques of a first inert gas which permits the determination of alveolar volume by detecting the dilution effect of the inert gas being inhaled into the lungs and then exhaled. A second gas, providing a means for monitoring an additional pulmonary function, is inhaled along with the inert gas and simultaneously monitored by the same infrared radiation techniques to provide an assessment of the additional function, for example pulmonary diffusing capacity or pulmonary blood flow.

In order to facilitate simultaneous monitoring of two or three selected gases, a sample cell is contemplated through which the gases are commonly inhaled and exhaled with continuous monitoring by means of infrared radiation. The sample cell is designed with limited volume for more rapid response and preferably includes pressure drop means for simultaneously determining the rate and volume of gas flow during inhaltion and exhalation. Finally, the gases employed for the various pulmonary functions being analyzed are carefully selected to have closely related but distinct infrared absorption bands to faclitate their simultaneous monitoring within the sample cell. Through the use of such a sample cell, a plurality of electronic channels may be employed to receive data for each of the gases in order to provide a signal output indicative of the respective pulmonary functions.

Additional objects and advantages of the invention will be made apparent in the following description having reference to the accompanying drawings.

BRIEF DESCRIPTION OF THE DRAWINGS

FIG. 3a is a table identifying various signals labeled by capital letters A through F in FIG. 3.

DESCRIPTION OF THE PREFERRED EMBODIMENTS

Figure 1:
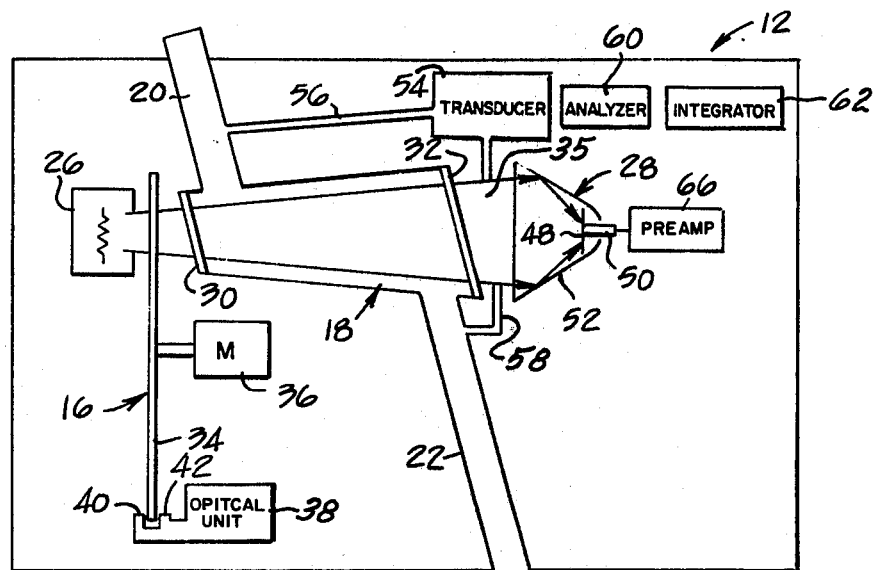
FIG. 1 is a partially sectioned, partially schematic representation of a pulmonary function analyzer device according to the present invention.

As indicated above, the present invention provides a method and apparatus for analyzing selected pulmonary functions by means of infrared radiation monitoring of a plurality of gases which are passed through the pulmonary function analyzer device of FIG. 1 during both inhalation and expiration from the lungs. As was also indicated above, the pulmonary function analyzer device of FIG. 1 may be employed to simultaneously and continuously monitor the concentrations of three different gases relating to three different pulmonary functions, preferably alveolar volume, pulmonary diffusing capacity and pulmonary blood flow. However, the pulmonary function analyzer device of FIG. 1 may also be employed to simultaneously perform two different pulmonary functions, preferably the function of determining alveolar volume and either pulmonary diffusing capacity or pulmonary blood flow.

Figure 2A:
FIG. 2a is a table identifying the various filter elements in the filter wheel of FIG. 2.
Figure 2:
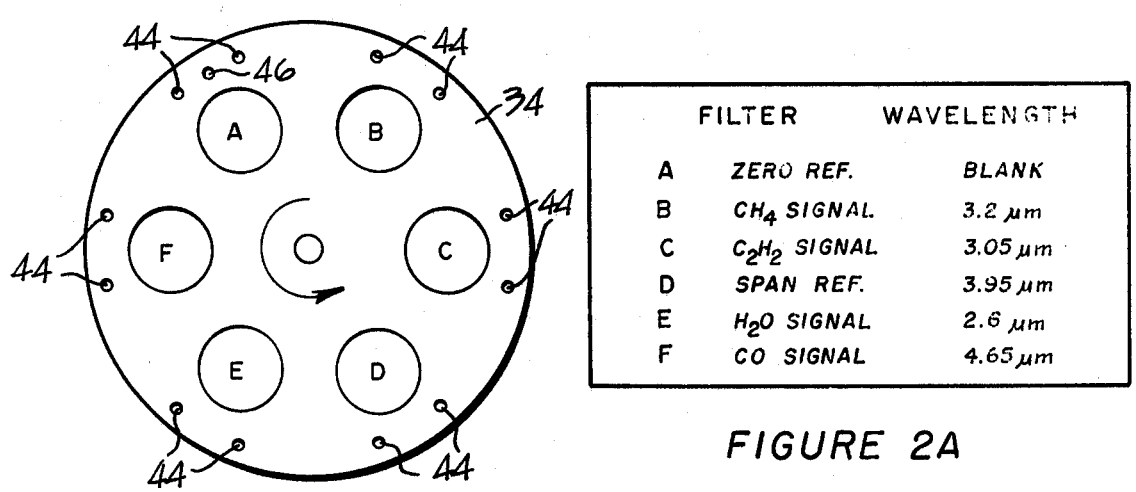
FIG. 2 is a fragmentary view of a filter wheel employed within the pulmonary function analyzer device of FIG. 1.
Figure 3:
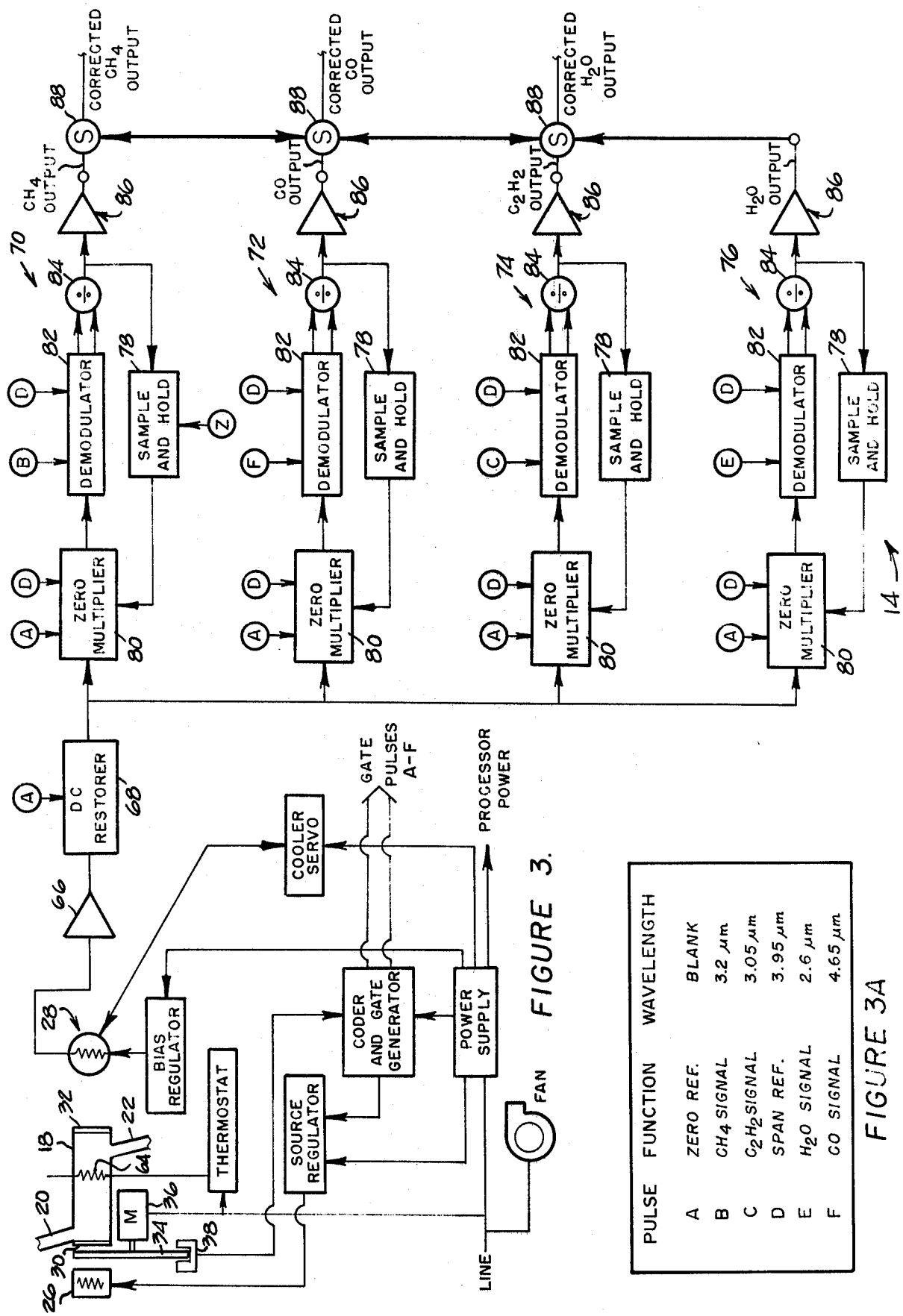
FIG. 3 is a schematic representation of an electronic processing unit associated with the pulmonary function analyzer device of FIG. 1.

The pulmonary function analyzer of the present invention preferably includes a separate optics unit indicated at 12 in FIG. 1 and an electronic processing unit indicated at 14 in FIG. 3. The electronic processing unit 14 includes generally conventional electronics components and circuits for receiving various signals porvided by the optics unit 12 of FIG. 1, processing those signals and providing an output or display effective to indicate the concentrations of the selected gases. The electronic processing unit 14 of FIG. 3 is described in greater detail below. However, the present summary of the invention is particularly concerned with the optics unit 12 of FIG. 1 and included components such as a filter wheel assembly 16 (see FIGS. 1 and 2) as well as the particular gases employed in combination within the present pulmonary function analyzer.

Generally, the optics unit 12 includes a shaped sample cell 18 which is interconnected with two separate conduits 20 and 22. The conduit 20 is adapted as a mouthpiece for the subject or patient to be tested by the pulmonary function analyzer. The other conduit 22 is of a branched configuration for alternately connecting the sample cell either with a gas supply 24 or a gas exhaust 25.

The optics unit 12 also includes a source of infrared radiation, indicated at 26, at one end of the sample cell 18. A detector assembly 28 is arranged at the other end of the sample cell in order to provide an instant and continuous analysis of gases within the sample cell 18. The filter wheel assembly 16 is mounted to selectively intercept the infrared radiation signal generated by the source 26.

In further summary as to operation of the pulmonary function analyzer device, the subject inhales through the mouthpiece 20 and draws a gas of selected composition from the supply 24 through the sample cell 18. The inhaled gas may be retained in the lungs of the subject for a selected period of time to permit uniform dilution of the inhaled gas throughout the lungs. Thereafter, the subject exhales again through the sample cell 18 with the exhaled gases either being exhausted through the outlet 25 or collected by suitable means (not shown) if it is desired to further analyze the exhaled gases.

In any event, the source 26 generates infrared radiation through the sample cell which is attenuated by the infrared absorption bands of gases in the sample cell 18 and thereafter received by the detector assembly 28. Thus, the detector assembly 28 generates an electrical signal providing a means of clearly and instantly identifying the concentration of the selected gases within the sample cell at all times during both inhalation and exhalation.

As noted above, the simultaneous analysis of gases in the sample cell 18 by the detector assembly 28 may be based upon three different gases relating to three different pulmonary functions such as alveolar volume, pulmonary diffusing capacity and pulmonary blood flow. However, the device may also be employed to simultaneously monitor any two of the gases, for example, those associated with alveolar volume and either pulmonary diffusing capacity or pulmonary blood flow.

As will be described in greater detail below, the detector assembly 28 may also be employed to additionally analyze the concentration of water vapor within the sample cell 18 in order to more accurately calibrate the output of the pulmonary function analyzer through the electronic processing unit 14 of FIG. 3.

Selection of Gases

The selection of the various gases employed within the pulmonary function analyzer of the present invention is of particular importance within the present invention. All of the gases relating to the various pulmonary functions must each exhibit an effective infrared radiation absorption band of usable strength in order to develop a response by the present pulmonary function analyzer. For example, the standard gases employed in the prior art for the measurement of the lung volume, such as helium, neon, and argon, do not absorb infrared radiation and accordingly may not be employed in the present pulmonary function analyzer.

In addition, each of the gases must exhibit the necessary reaction within the lungs for providing an indication of the particular pulmonary function to be monitored. An analysis of the particular gases employed in the pulmonary function analyzer is set forth immediately below. However, it is first generally noted that the composite gas being exhaled by a patient or subject may include other gases from the lungs which must also be considered in the design of the pulmonary function analyzer. For example, certain gases which are commonly present in the lungs tend to interfere with infrared detection of the selected gases. Accordingly, the selected gases identified with the various pulmonary functions are also selected to permit monitoring of varying concentrations thereof even in the presence of such interferent gases.

At the same time, the gases associated with the various pulmonary functions must also be considered as interferent gases relative to each other. Accordingly, the selected gases must generally have distinct absorption bands or wave lengths so that they will not interfere with each other.

Finally, it is also important to ascertain the combined wave length or absorption band for all of the gases associated with the various pulmonary functions. If the combined absorption band of the gases is overly broad, the design of the optics unit 12 may tend to be complex. For example, the use of selected gases with a very broad band of wave lengths might require the inclusion of beam splitter means in the optics unit for separating different ranges of wave lengths which would then be analyzed by separate detector assemblies.

Returning again to the selection of the gases associated with the varous pulmonary functions, a gas for determining alveolar volume must be inert while exhibiting a useful absorption band for infrared radiation in accordance with the preceding comments. As noted above, the usual inert gases such as helium, neon and argon may not be employed since they do not absorb infrared radiation. However, two exemplary inert gases exhibiting infrared absorption bands are sulfur hexafluoride ($SF_6$) and methane ($CH_4$).

Sulfur hexafluoride exhibits a detectable absorption band for infrared radiation. Tests with a pulmonary function analyzer device have indicated the feasability of employing sulfur hexafluoride for determining alveolar volume. However, it has also been found that the absorption band of sulfur hexafluoride is not at a wavelength which can be detected by the same detector used for carbon monoxide. A separate special detector could be and has been used to detect sulfur hexafluoride. However, it has been found more expedient to employ methane for monitoring this pulmonary function.

A careful study has indicated that methane satisfies both the physiological and detection criteria for use in the present invention. Methane exhibits a strong infrared radiation absorption band centered at 3.2 $\mu m$ (millimicrons) which absorption band is substantially free from interference caused by water vapor and carbon dioxide, two of the interferent gases present in the lungs.

Some overlap exists between the absorption band for methane and the absorption band typical of longer chain hydrocarbons which lie in the general absorption band of 3.3 to 3.7 $\mu m$. Of such hydrocarbon compounds, only ethanol ($C_2H_5OH$) appears to provide any potentially significant interference. However, a more detailed investigation of the interaction between the spectra for ethanol and methane indicates that any such interference is relatively insignificant in the results provided by the present pulmonary function analyzer. Also, the problem of interference with ethanol may be controlled to some degree by limiting the consumption of alcohol prior to conducting tests with the present pulmonary function analyzer.

As for the physiological effect of methane, it is relatively insoluble either in water or hemoglobin and is therefore not substantially diffused through the alveolar capillary walls.

For the monitoring of pulmonary diffusing capacity, it is initially noted that a completely different physiological effect is required of a gas employed for this purpose. Initially, the gas must tend to be readily absorbed by hemoglobin so that its absorption in the blood will not be a relatively limiting factor determining its diffusion from the lungs. Rather, the gas should also exhibit a relatively controlled but well characterized rate of absorption or diffusion through the alveolar capillary walls. In this manner, the rate of flow for the gas from the lungs tends to be directly proportional with the function of pulmonary diffusing capacity and thus an effective means for monitoring that function.

As discussed in some detail above, cyanide compounds may also be employed for monitoring this particular pulmonary function. However, because of certain problems associated with the monitoring of cyanides, carbon monoxide is preferred for use within the pulmonary function analyzer of the present invention.

Figure 4:
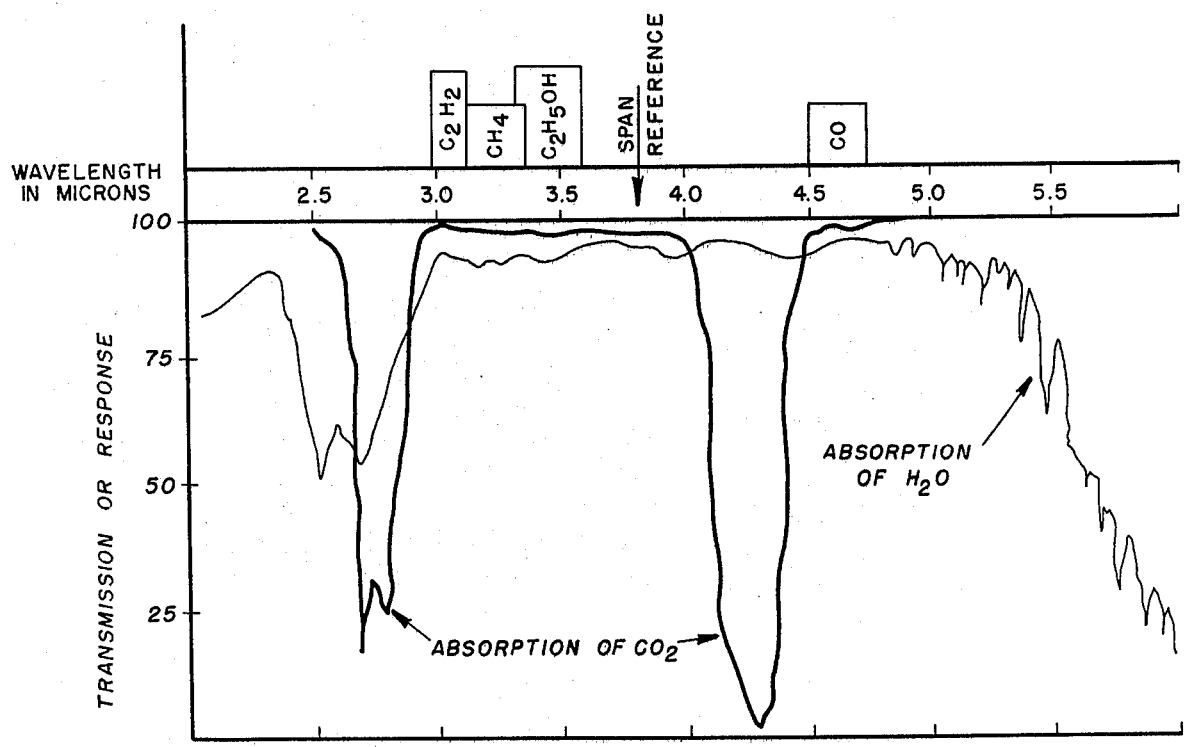
FIG. 4 is a graphical representation of the infrared spectrum for selected gases employed in the pulmonary function analyzer device of FIG. 1 along with selected interference gases.

As may be seen by reference to FIG. 4, the infrared radiation absorption band for carbon monoxide is approximately 4.5 to 4.75 $\mu m$. Accordingly, carbon monoxide in a preferred maximum concentration of about 0.3% is employed within the gas supply indicated at 24 in FIG. 1. Such a concentration has been found to exhibit acceptably low toxicity for use in the manner of the present invention.

Finally, in assessing or monitoring the function of cardiac output or pulmonary bloodflow, acetylene ($C_2H_2$) is particularly contemplated for use within the present invention. Acetylene has been found to ideally exhibit the desired physiological effects for monitoring this function. In particular, acetylene has well characterized solubility in blood. In addition, acetylene is readily diffused through the alveolar capillary walls or surfaces of the lungs so that dissipation of acetylene from the lungs may be directly correlated with capillary blood flow in the lungs. In addition, acetylene is otherwise effectively inert, so that its solubility would not be influenced by hematocrit. At the same time, acetylene is effectively incapable by itself of influencing pulmonary blood.

Other gases such as nitrous oxide and ethylene have been considered for monitoring this function because of their intermediate solubility in blood and lung tissue. However, certain problems have been found in connection with each of these gases so that acetylene is preferred. For example, nitrous oxide is one of the few gases which strongly interferes with carbon monoxide detection by means of infrared radiation.

Some minor problems have been found, for example, in connection with acetylene storage since the gas tends to leak through rubber which is commonly employed within such devices. However, this problem may be readily controlled through the use of suitable linings within the pulmonary function analyzer device of the present invention and associated components.

Acetylene also satisfies the spectral criteria of the present invention since the primary infrared radiation absorption band centered at approximately 3.5 μm lies well within an "interference-free" window as illustrated in FIG. 4. In particular, the spectrum of acetylene does not significantly overlap that of methane and with a judicious choice of filter specifications and electronics compensation in the circuitry described below, total separation of the signals for these two gases may be effectively achieved.

The preceding description is intended to establish the preferred selection of methane, carbon monoxide and acetylene for measuring the respective pulmonary functions of alveolar or lung volume, pulmonary diffusing capacity and pulmonary blood flow. In order to more clearly illustrate the associated absorption bands for these three gases, reference is again made to FIG. 4 wherein the absorption bands for the three gases are illustrated in conjunction with representations of the major absorption regions for the dominant interferent gases, carbon dioxide and water vapor. Also, it may be seen from FIG. 4, that the overall combined band width of approximately 3 to 4.7 μm which includes all of the above three gases, is of sufficiently limited scope to permit detection of infrared radiation absorption for all three gases by means of a single detector unit as indicated at 28 in FIG. 1.

Description of Optics Unit (FIG. 1)

Referring now to FIG. 1, it was noted above that gas ports or conduits 20 and 22 are provided at opposite ends of the same cell 18. The conduit 20 provides a mouthpiece while the conduit 22 provides alternate communication with either an exhaust or a source of gas supply.

Optical windows 30 and 32 formed for example from calcium fluoride or sapphire are arranged at opposite ends of the sample cell to provide an enclosure therebetween for the passage of inhaled and exhaled gases. The window 30 is arranged adjacent the source 26 and the chopper wheel assembly 16 while the other window 32 is arranged adjacent the detector assembly 28.

The manner of generating and detecting a number of IR band widths is commonly referred to as the "filter wheel" technique. Briefly, the filter wheel assembly 16 includes a chopper wheel 34 which is rotatable by motor means 36. As may be more clearly seen in FIG. 2, the chopper wheel 34 mounts six filter elements respectively identified as A, B, C, D, E and F. The function of these various filters is described below. However, the filters are arranged so that upon rotation of the chopper wheel 34, they intersect or are periodically aligned between the IR source 26 and the sample cell 18.

The filters B, C and F correlate with the absorption bands for the respective gases $CH_4$, $C_2H_2$, and CO, the filter pass band for the filters being selected to include a strong absorption band of the associated gas to be detected.

In addition, the filter D provides a span reference at a wave length which is not absorbed by any of the three test gas components. The reference pulse from the filter D is electronically employed to provide an overall transmission amplitude or span reference which renders the instrument insensitive to variations in window transmission, sample cell reflectivity, etc. As will be made apparent in the discussion of the electronic processing unit 14 illustrated in FIG. 3, the span reference pulse is employed as a reference base for correcting or calibrating the signal output for the three filters B, C and F.

An opaque plate at filter position A is employed to provide a zero beam reference for the measurement of the radiation pulse amplitude from the three filters B, C and F. The zero reference pulse provided at the position A is required since the radiation pulses from the other filters tend to follow each other so closely that there may be insufficient spacing between them for the effective establishment of a noise-free zero reference.

The filter E is selected to cover the band width for water vapor. Although the pulmonary function analyzer of the present invention particularly contemplates monitoring of the three gases carbon monoxide, methane and acetylene, it also preferably monitors water vapor as well in order to provide a corrections factor for those three gases in order to more accurately calibrate the output signals from the pulmonary function analyzer. The filter E permits an interference-free measurement of water concentration at the wave length of 2.6 μm with a band width of 0.07 μm in order to avoid parasitic response to the $CO_2$ band at 2.7 μm (see FIG. 4).

It is incidentally noted that, rather than providing a similar filter for monitoring $CO_2$ concentration, it is possible to substantially reduce instrument response to $CO_2$ by inserting a $CO_2$ absorbing cell (not shown) in the optical path. This could be accomplished, for example, by filling the chamber 35 formed between the window 32 and the detector assembly 28 with carbon dioxide ($CO_2$) or any other selected interferent gas. In this manner, all infrared radiation which would be susceptible to absorption because of the presence of the selected interferent gas in the sample cell is removed in order to permit more accurate detection of gases in the sample cell. Carbon dioxide is of particular concern since it is commonly present in an expired gas mixture.

An optical pick-up unit 38 is also associated with the chopper wheel 34 for synchronizing pulses from each of the filters A-F with the electron processing unit 14. The optical pick-up unit 38 includes a light emitting diode means 40 on one side of the chopper wheel 34 with a photo transistor 42 being arranged upon the side of the chopper wheel 34. Referring momentarily to FIG. 2, it may be seen that a pair of pick-up holes 44 is associated with each of the filters. As each of the pick-up holes passes the optical unit 38, the photo transistor 42 is actuated by the light emitting diode 40 to produce a synchronizing signal for the electronic processing unit 14.

In order to assure that counter means (not otherwise shown) within the electronic processing unit 14 remain in synchronization with the chopper wheel 34, a reset pulse is generated by a single reset hole 46 provided adjacent the center of the filter position A. Thus, a reset pulse succeeds the start pulse for the filter position A more rapidly than any other pulse in the entire cycle. This reset pulse may be distinguished for example by means of a timer and coincident circuit (not shown) to generate the counter reset pulse.

The reset unit also serves a safety function of protecting the filter wheel from steady infrared radiation which would become destructively intense for any of the filters A-F if the chopper wheel 34 were to stop rotating for any reason. Upon such an occurrence, the reset pulse would not be generated. The source generator 26 is designed to turn off if the reset pulse is absent for more than a few seconds in order to protect the filters A–F.

As indicated above, the band widths for the three gases CO, $CH_4$, and $C_2H_2$ permit detection by a single detector assembly 28. The detector assembly 28 preferably comprises a lead-selenium (PbSe) detector having a suitable band width for the three gas channels. The lead-selenium detector is indicated at 48 in FIG. 1. The normal operating temperature for the detector 48 is approximately $-20°$ centigrade. This temperature is preferably maintained for example by means of a small semi-conductor type cooler unit built into the detector mounting 50. The cooling unit receives power from the instrument power supply through a conventional thermistor controlled temperature regulating circuit (not shown). An ellipsoidal radiation collector 52 is mounted around the detector 48 and assists the detector 48 in detecting a large fraction of the IR radiation which is transmitted through the sample cell 18.

In addition, the sample cell 18 includes a number of additional features to enhance operation of the pulmonary function analyzer. For example, the internal volume of the sample cell 18 and the conduits 20 and 22 is limited as much as possible in order to increase the response time for the analyzer.

At the same time, it is noted that operating parameters for the infrared source 26 and the detector assembly 28 may be accurately calibrated to accommodate either turbulent or laminar flow conditions within the sample cell 18. However, in normal use turbulent flow is expected to be encountered under all normally rapid exhalations. It is also generally desirable that the subject exhale rapidly during use of the pulmonary function analyzer in order to avoid abnormal patterns of air flow from the lungs and to provide a reproducible air flow pattern. Accordingly, the design of the sample cell 18 is preferably configured for the purpose of inducing turbulent flow conditions therein at all times to permit constant calibrations for the detector 28. For this reason, the sample cell 18 is formed as a truncated pyramidal section with the conduit 20 being interconnected with the smaller end thereof. At the same time, the conduit 20 is arranged at an angle of approximately 60° to 75° relative to the center-line of the sample cell 18. The conduit 22 is arranged generally parallel with the conduit 20 as are the windows 30 and 32. With such an arrangement, exhalation flow from the conduit 20 tends to rapidly fill the sample cell 18 and induce turbulent flow conditions at the same time. Thus, the design of the sample cell along with the conduits 20 and 22 is selected both for the purpose of increasing the response time of the pulmonary function analyzer as well as making it more uniformly responsive to concentrations of the selected gases within the sample cell 18.

It was also noted above that it is additionally necessary to closely monitor the volume of flow through the sample cell 18 both during inhalation and exhalation in order to accurately determine alveolar volume. Within the embodiment of FIG. 1, the flow measurement is accomplished by measurement of a pressure drop induced by the above-noted configuration of the sample cell and the conduits 20 and 22. Because of the arrangement of these components as noted above, a pressure drop is developed between the conduits 20 and 22 which is measured by a pressure differential transducer having side arms 56 and 58 interconnected with the respective conduits 20 and 22. In order to provide a signal corresponding to flow volume through the sample cell 18, the transducer 54 is interconnected with a logarithmic function analyzer 60 for generating an analog signal proportional to flow volume through the cell 18. The analyzer 60 is in turn connected with an electronic integrator 62 which integrates the flow analog signal over a period of time for either inhalation or exhalation in order to provide an indication of inhaled or exhaled volume. Although this is a preferred means for measuring flow other means such as a pneumotach could also be employed along one of the conduits 20 or 22.

Accordingly, the optics unit 12 of FIG. 1 is effective to sequentially provide pulse signals corresponding to alignment of the filters A–F between the infrared source 26 and the detector assembly 28. Further, the optics unit 12 supplies a signal from the integrator 62 which corresponds to flow volume through the sample cell 18. These signals are delivered to the electronic processing unit 14 of FIG. 3 which, as noted above, includes generally conventional processing circuits for analyzing signals received from the optics unit and providing a suitable display thereof.

Electronic Processing Unit (FIG. 3)

Referring now to FIG. 3, a block diagram of the electronic processing unit 14 is illustrated along with a schematic representation of various components described above for the optics unit 12. As was indicated above, the optics unit 12 and electronic processing unit 14 are constructed separately in order to facilitate use during pulmonary testing and to permit access to the optics unit for example to clean the sample cell.

Various electrical components contained within the optics unit or head include the infrared source 26, the drive motor 36 for the chopper wheel, the detector assembly 28 and a sample cell temperature regulator generally indicated at 64 in FIG. 3 for maintaining the temperature of the sample cell at approximately body temperature in order to avoid fogging within the sample cell and to also avoid undesirable effects of temperature variation during monitoring of the selected gases. In accordance with normal practice, a signal preamplifier 66 is mounted close to the detector assembly 28 in order to minimize noise pick-up, the preamplifier serving to communicate output pulses from the detector assembly 28 to the electronic processing unit 14.

Various electrical components for regulating operation of components within the optics unit include special regulators for controlling the detector bias and the thermal electric cooler for the detector (see FIG. 3). Also, the electronics unit includes conventional DC power supplies, regulator means for the infrared source 26 and decoder and pulse generator means for generating the synchronous gate pulses from signals received from the optical pick-up 38. As described above, the optical pick-up 38 itself is mounted adjacent the rim of the chopper wheel 34 in the optics unit.

As for the electronic processing unit 14, it is noted that numerous circuit arrangements may be employed in order to receive the electrical data described above from the optics unit 12 and to process it for analysis by an operator. FIG. 3 illustrates one combination of circuitry capable of performing this function.

As will be apparent from the preceding description, the signal emerging from the preamplifier 66 consists of a train of five pulses associated with the filters B–F followed by a space corresponding to the filter A where no signal exists.

This signal arrangement from the preamplifier 66 is first communicated to a common DC restorer 68. The above-noted space or pulse associated with the filter A is used as a gate to restore the DC base line within the restorer 68, thereby permitting the remainder of the electronic processing unit 14 to measure absolute signal amplitudes for the pulses received from the optics unit in connection with the other filters B-F.

Beyond the restorer 68, the electronic unit 14 includes a series of branched circuits for analyzing each of the gases monitored in the sample cell along with an additional similar branched circuit for receiving a circuit corresponding to water vapor in the sample cell. These branched circuits are referred to respectively at 70, 72, and 74 and 76 and relate respectively to signals for the gases methane, carbon monoxide, acetylene and water vapor. Each of the branched circuits 70-76 includes similar components except for the signals to which each of the branched circuits is responsive. Those signals are indicated by capital letters corresponding to pulses received for the individual filters described above in conjunction with FIGS. 1, 2 and 2a.

Each analysis of pulmonary function is commenced with initiation of auto-zero cycle with zero gas in the sample cell 18, the cycle causing an auto-zero feedback loop in each of the circuits of channels 70-76 to add to or substract from the span reference pulse until the DC output is zero. Each feedback loop consists of a sample-and-hold circuit 78 and a zero multiplier 80. During the abovenoted cycle the negative feedback loop seeks a null in the output of the divider 84, developing a correction voltage which is sorted in the sample-and-hold circuit 78 for each channel or circuit 70-76 and is applied as a correction until a subsequent sample-and-hold cycle is initiated. As noted above, such a subsequent sample-and-hold cycle is initiated upon recommencement of the pulmonary function analysis either for the same subject or for a different subject.

As indicated in FIG. 3, each zero multiplier 80 is responsive to the pulses from the filters A and D. During operation of the pulmonary function analyzer in the analysis mode following the auto-zero cycle, the multiplier 80 responds to the sample-and-hold circuit 78 to correct the signal received from the DC restorer 68.

This correction factor is applied to a demodulator which is again responsive to both the span reference signal from the filter D and to the methane signal from the filter B. The demodulator is indicated in each of the branched circuits or channels 70-76 at 82. Signal and reference outputs from the demodulator 82 are applied to the divider circuit 84 which ratios the methane signal from filter B to the span reference signal from filter D in order to provide an output signal corresponding to methane sensed in the sample cell 18 (see FIG. 1). That output signal is in turn applied to a linearizing amplifier 86 which thus modifies the signal monitored through filter B in accordance with the physical law of absorption of radiation related to the concentration of methane in the sample cell. The other circuits 72, 74, and 76 similarly function to provide a corrected output signal indicative of the presence of carbon monoxide, acetylene and water vapor respectively within the sample cell. The output from the final circuit 76 for water vapor is applied through summing means 88 in order to accomplish the above-noted function of correcting the signal outputs for the circuits 70, 72, and 74 to minimize sensitivity thereof to water vapor in the sample cell.

Accordingly, there has been described a novel pulmonary function analyzer providing a rapid response for simultaneously monitoring two or more gases relating to different pulmonary functions. It will be obvious that numerous changes and modifications may be made in addition to those described above. Accordingly, the scope of the present invention is defined only by the following appended claims.

What is claimed is:

1. A method for non-invasively and continuously monitoring the three different pulmonary functions of alveolar volume, pulmonary diffusing capacity and pulmonary blood flow, comprising the steps of
   providing a known volume of a gas including known concentrations of first, second and third selected gases for inhalation by a subject,
   selecting the first gas as an inert gas having a measurable infrared absorption band,
   selecting the second gas to also have a measurable infrared absorption band and a relatively high affinity for hemoglobin with a measurable rate of absorption or diffusion through alveolar capillary walls in order to monitor the function of pulmonary diffusing capacity,
   selecting the third gas to also have a measurable infrared absorption band, the third gas also being selected to readily diffuse through alveolar capillary surfaces or walls of the lungs while having a measurable degree of solubility in blood in order to monitor the pulmonary function of capillary blood flow,
   causing the subject to inhale said first, second and third gases,
   thereafter passing expiration gases from the subject through a sample cell,
   simultaneously detecting the concentrations of said first, second and third gases in said sample cell by directing infrared radiation through said sample cell and detecting the amount of absorption due to each of said first, second and third gases, and
   measuring the volume of gas exhaled by the subject in order to determine alveolar volume by means of the detected first gas concentration while simultaneously monitoring the pulmonary functions of diffusing capacity and capillary blood flow by means of the detected second and third gas concentrations.

2. The method of claim 1 wherein said first, second and third gases are further selected to have infrared absorption bands which are relatively distinct from each other and from interferent gases normally found in the lungs.

3. The method of claim 2 wherein said first gas is methane, said second gas is carbon monoxide and said third gas is acetylene.

4. A method for analyzing different pulmonary functions including alveolar volume and a second pulmonary function, comprising the steps of
   providing a known volume of gas with known concentrations of first and second selected gases for inhalation by a subject;
   selecting the first gas as an inert gas having a measurable infrared absorption band,
   selecting the second gas to also have a measurable infrared absorption band, the second gas also being effective to provide an indication of a second pulmonary function, causing a subject to inhale the first and second gases, thereafter passing expiration gases from the subject through a sample cell, simultaneously detecting the concentrations of said first and second gases in said sample cell by directing infrared radiation through said sample cell and detecting the amount of absorption due to said first and second gases, and measuring the volume of gas exhaled by the subject in order to simultaneously determine alveolar volume by means of the first gas detected concentration and monitor said second pulmonary function by means of the detected second gas concentration.

5. The method of claim 4 wherein said second gas is selected to have relatively high affinity for hemoglobin and a measurable rate of absorption or diffusion through alveolar capillary walls in order to monitor the pulmonary function of diffusing capacity thereby.

6. The method of claim 5 wherein said first gas is methane and said second gas is carbon monoxide.

7. The method of claim 4 wherein said second gas readily diffuses through alveolar capillary surfaces or walls of the lungs while having a measurable degree of solubility in blood in order to monitor the pulmonary function of capillary blood flow.

8. The method of claim 7 wherein said first gas is methane and said second gas is acetylene.

9. The method of claim 4 further comprising the steps of simultaneously monitoring the concentration of water vapor within the sample cell by detecting the amount of infrared absorption thereby in order to correct any error in the measurement of said first and second gases because of interference due to said water vapor.

10. The method of claim 4 further comprising the steps of also directing the infrared radiation through an enclosed quantity of an interferent gas prior to the detection of infrared absorption, the interferent gas being selected as a gas capable of appearing in the sample cell and interfering with the proper detection of said first and second gases.

11. The method of claim 10 wherein said interferent gas is carbon dioxide.

12. The method of claim 11 wherein said first gas is methane and said second gas is carbon monoxide.

13. The method of claim 4 further comprising the steps of selecting a third gas to have a measurable infrared absorption band relatively distinct from the absorption bands for said first and second gases, causing the subject to inhale said third gas along with said first and second gases, simultaneously detecting the concentration of said third gas along with the concentrations of said first and second gases in said sample cell, and monitoring a third pulmonary function by means of the detected third gas concentration simultaneously with the determination of alveolar volume by means of the detected first gas concentration and the monitoring of said second pulmonary function by means of the detected second gas concentration.

14. The method of claim 13 wherein said second gas is selected to have relatively high affinity for hemoglobin and a measurable rate of absorption or diffusion through alveolar capillary walls in order to monitor the pulmonary function of diffusing capacity, said third gas being selected to readily diffuse through alveolar capillary surfaces or walls of the lungs while having a measurable degree of solubility in blood in order to monitor the pulmonary function of capillary blood flow.

15. The method of claim 14 wherein said first gas is methane, said second gas is carbon monoxide and said third gas is acetylene.

16. The method of claim 14 comprising the additional step of also detecting the concentration of water vapor in the sample cell and correcting errors in the measurement of said first, second and third gases due to interference from water vapor.

17. A pulmonary function analyzer for simultaneously and continuously monitoring the three pulmonary functions of alveolar volume, pulmonary diffusing capacity and pulmonary blood flow comprising a source containing first, second and third selected gases, said source including means for permitting inhalation into a subject's lungs of a known composite gas volume including known concentrations of the first, second and third selected gases, the first gas being an inert gas having a measurable infrared absorption band, the second gas having a measurable infrared absorption band and a relatively high affinity for hemoglobin with a measurable rate of absorption or diffusion through alveolar capillary walls in order to monitor the function of pulmonary diffusing capacity, the third gas also having a measurable infrared absorption band, the third gas also being readily diffusible through alveolar capillary surfaces or walls of the lungs while having a measurable degree of solubility in blood in order to monitor the pulmonary function of capillary blood flow, a sample cell including an infrared source of radiation and an infrared detector means arranged at opposite ends thereof to continuously monitor the concentrations of said gases within said sample cell, inlet means for permitting flow of said gases exhaled by the subject into said sample cell, outlet means for allowing said flow of gases to exit from said sample cell, means for measuring the composite gas volume exhaled by the subject through said sample cell, and means responsive to said infrared detector means and responsive to said means for measuring composite gas volume for simultaneously monitoring alveolar volume, pulmonary diffusing capacity and pulmonary blood flow.

18. The pulmonary function analyzer of claim 17 wherein said inlet means comprises a conduit including a mouthpiece, said outlet means including a conduit for connecting the sample cell with an exhaust means to permit the monitoring of gases being passed through the sample cell from the mouthpiece toward the exhaust means.

19. The pulmonary function analyzer of claim 18 further comprising means for alternately connecting said conduit of said outlet means with said source so that said selected gases may pass through said sample cell toward the mouthpiece during inhalation while continuously monitoring the concentrations of said gases during both inhalation and expiration.

20. The pulmonary function analyzer of claim 19 further comprising electronic processing means for processing signals passing from said infrared detector means in order to continuously and instantaneously monitor the concentrations of selected gases in said gas flow through said sample cell during both inhalation and expiration.

* * * * *